United States Patent
Torrie et al.

[19]

[11] Patent Number: 6,146,385
[45] Date of Patent: *Nov. 14, 2000

[54] REPAIRING CARTILAGE

[75] Inventors: Paul A. Torrie, Marblehead; Michael C. Ferragamo, N. Dighton, both of Mass.; Rebecca Blough, Warwick, R.I.; Anthony Miniaci, Thornhill, Canada; Lázló Hangody; Zoltán Kárpárti, both of Budapest, Hungary

[73] Assignee: Smith & Nephew, Inc., Andover, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/799,697

[22] Filed: Feb. 11, 1997

[51] Int. Cl.$^7$ ................................................. A61B 17/17
[52] U.S. Cl. ............................... 606/96; 606/80; 606/88; 606/99
[58] Field of Search ................................ 606/96, 97, 98, 606/86, 99, 102, 80, 79, 83, 84, 85, 76, 72, 60, 53

[56] References Cited

U.S. PATENT DOCUMENTS

| | | | |
|---|---|---|---|
| 4,349,058 | 9/1982 | Comparetto | 606/84 |
| 4,708,139 | 11/1987 | Dunbar, IV | 606/96 |
| 4,710,075 | 12/1987 | Davison | 606/80 |
| 5,163,940 | 11/1992 | Bourque | 606/96 |
| 5,190,548 | 3/1993 | Davis | 606/80 |
| 5,207,681 | 5/1993 | Ghadjar et al. | 606/96 |
| 5,269,785 | 12/1993 | Bonutti | 606/80 |
| 5,405,348 | 4/1995 | Anspach, Jr. et al. | 606/80 |
| 5,484,437 | 1/1996 | Michelson | 606/61 |
| 5,489,307 | 2/1996 | Kuslich et al. | 623/17 |
| 5,490,852 | 2/1996 | Azer et al. | 606/79 |
| 5,569,262 | 10/1996 | Carney | 606/96 |
| 5,573,537 | 11/1996 | Rogozinski | 606/80 |
| 5,575,794 | 11/1996 | Walus et al. | 606/116 |
| 5,603,716 | 2/1997 | Morgan et al. | 606/88 |
| 5,632,745 | 5/1997 | Schwartz | 606/75 |
| 5,785,714 | 7/1998 | Morgan et al. | 606/86 |
| 5,919,196 | 7/1999 | Bobic et al. | 606/86 |
| 5,951,559 | 9/1999 | Burkhart | 606/73 |

FOREIGN PATENT DOCUMENTS

| | | |
|---|---|---|
| 0307241 | 3/1989 | European Pat. Off. . |
| 0508710 | 10/1992 | European Pat. Off. . |
| 0824893 | 2/1998 | European Pat. Off. . |
| 19503504A1 | 3/1996 | Germany . |
| 96/24302 | 8/1996 | WIPO . |
| 96/27333 | 9/1996 | WIPO . |

OTHER PUBLICATIONS

Vladimir Bobic, M.D.; "The Utilization of Osteochondral Autografts in the Treatment of Articular Cartilage Lesions"; The Arthrex Solution to Osteochondral Autograft Transfer System (OATS™); AAOS 65$^{th}$ Annual Meeting, New Orleans, Mar. 29–23, 1998; Instructional Course No.: 146 (12 pages).

(List continued on next page.)

*Primary Examiner*—Michael Buiz
*Assistant Examiner*—David O. Reip
*Attorney, Agent, or Firm*—Fish & Richardson, P.C.

[57] ABSTRACT

A method of repairing cartilage (e.g., articular cartilage on the femur) and a set of instruments used in the method are provided. The damaged cartilage is removed from the bone to expose the underlying bone, grafts covered with cartilage (e.g., hyaline cartilage) are harvested from elsewhere in the body (e.g., other areas of the femur), and the grafts are inserted into holes drilled into the exposed area of bone. A guide is provided for use with surgical instruments during the procedure to orient the surgical instruments perpendicularly to the bone surface during use. The guide includes a guiding portion disposed along a longitudinal axis for engaging the surgical instrument, and a tissue-engaging portion oriented perpendicularly to the longitudinal axis. A set of surgical instruments used to carry out the method includes the guide, a drill for forming the graft-receiving holes, and an insertion tool for inserting the grafts. Other accessory instruments are also provided.

62 Claims, 10 Drawing Sheets

OTHER PUBLICATIONS

Arthrex, "Finally, An Arthroscopic Treatment for Osteachondral Lesions," Arthroscopic Osteachondral Auto–Graft Transplantation in ACL Reconstruction: A Preliminary Clinical Study, 1996.

Beadling et al., "World of Opportunity for Osteochondral Transplantation," Sports Medicine, Sep. 1996.

Innovasive, "Innovasive COR System", Ordering Information, Sep. 1996.

Innovasive, "Innovasive COR System Components", Innovasive COR Repair System, Catalog No. 3510, Oct. 1996.

Innovasive, "Innovasive COR System: An Arthroscopic Technique for Harvesting & Transplanting Bone Grafts", Innovasive Instructional Technique, Sep. 1996.

Innovasive, Instructional Insert Innovasive COR System, Doc. #50000276 rev. A.

Instrument Maker, "Biologically Quiet, Superior Biodegradable Implants for ACL Reconstruction", 1996 Catalog, p. 22.

Kalb et al., "Hope for Damaged Joints", Newsweek, Medicine, Jan. 29, 1996, p. 55.

Matsusue et al., "Arthroscopic Multiple Osteochondral Transplantation to the Chondral Defect in the Knee Associated with Anterior Cruciate Ligament Disruption", Jour. Arth. & Related Surg. 9(3), 1993, pp. 318–321.

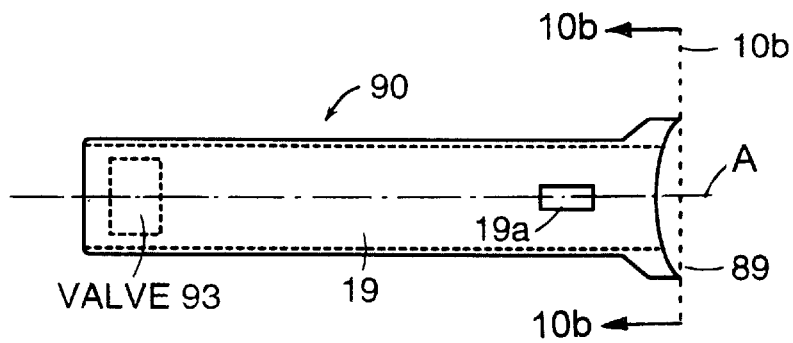
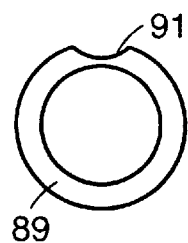
FIG. 10a  FIG. 10b
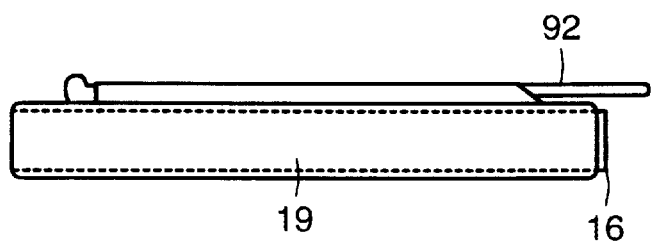
FIG. 11a
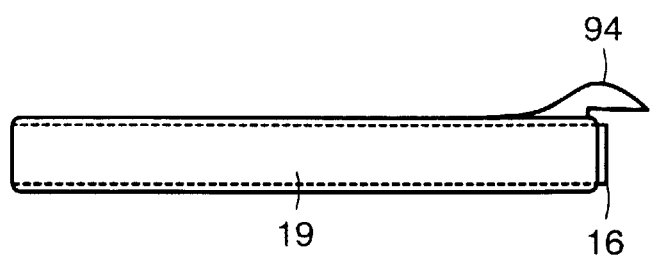
FIG. 11b
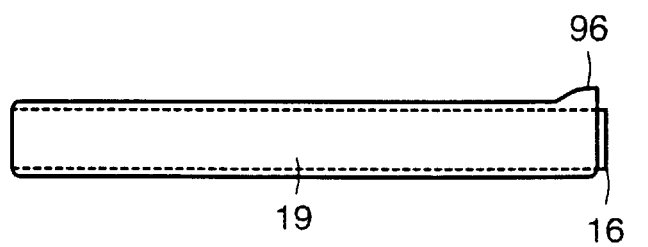
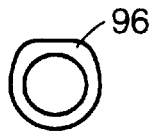
FIG. 11c

REPAIRING CARTILAGE

BACKGROUND

This invention relates to repairing cartilage, for example, articular cartilage on the femur.

Articular cartilage that is damaged (e.g., torn or excessively worn) may be repaired in a variety of ways. For example, the damaged cartilage may be shaved or scraped from the bone surface, thereby causing bleeding which stimulates the growth of fibrocartilage. Small holes may be drilled in the bone to promote bleeding and fibrocartilage growth. Alternatively, an allograft (e.g., cartilage grown in vitro from cartilage tissue removed from the patient) may be implanted by attaching a periosteum membrane (harvested, e.g., from the patient's tibia), to the bone surface and injecting the allograft beneath the membrane. The periosteum provides a healthy environment which promotes further cartilage cell growth.

SUMMARY OF THE INVENTION

This invention features, in general, a method of repairing cartilage—and a set of instruments used in the method—by removing the damaged cartilage from the bone to expose the underlying bone, harvesting grafts covered with cartilage from elsewhere in the body, and inserting the grafts into holes drilled into the exposed area of bone. The invention is particularly useful (but by no means exclusively so) in repairing damaged articular cartilage on the femur with bone grafts covered with hyaline cartilage that are harvested from another area of the femur.

One general aspect of the invention features a guide for use with surgical instruments during the procedure to orient the surgical instruments perpendicularly to the bone surface during use. The guide includes a guiding portion disposed along a longitudinal axis for engaging the surgical instrument, and a tissue-engaging portion oriented perpendicularly to the longitudinal axis.

Preferred embodiments may include one or more of the following features.

The surgical instruments used with the guide include a drill for drilling a hole for receiving the tissue graft, a dilator having a distal end sized to enlarge the hole, and an insertion tool for inserting the tissue graft into the hole. The guiding portion of the guide is sized to receive each instrument and orient it perpendicularly to the bone surface. Preferably, the tissue graft includes bone with a layer of cartilage thereon.

Preferably, the drill includes a distal end that comprises a pointed distal tip and a plurality of cutting flutes circumferentially spaced around the distal end proximally adjacent to the tip. The drill includes markings to indicate a depth of the hole. The distal end of the dilator is preferably tapered, and the dilator includes markings to indicate the depth that the distal end is inserted in the hole.

The portion of the insertion tool engaged by the guide has an adjustable length relative to the length of the guide so that the amount by which the graft protrudes from the hole can be correspondingly adjusted. The length-adjustable portion of the insertion tool includes a rod attached to a handle configured to engage a proximal end of the guide. The distal end of the rod is configured to engage the graft, and the proximal end of the rod is progressively insertable into an opening in the handle to adjust the length of the rod.

For example, the proximal end of the rod is threadably received within the opening so that relative rotation between the handle and the rod adjusts the length of the rod. A resilient member disposed in the opening engages the proximal end of the rod to maintain the rod in position at the adjusted length. The rod includes markings to indicate the amount by which the graft protrudes from the hole.

The guide may have a wide variety of suitable configurations. Preferably, the guide comprises a tube having a passage disposed along the longitudinal axis to provide the guiding portion. The tissue-engaging portion is disposed at a distal end of the tube and is, for example, a rim of the tube. In some embodiments, the tissue-engaging portion also includes an annular flange that projects distally from the rim and is configured to be seated within the bone tissue. In other embodiments, the tissue-engaging portion comprises an enlarged lip disposed circumferentially around the distal end of the tube. A portion of the lip may include a recess therein.

The guide may also include a spacer for positioning the guiding portion at a selected location relative to a feature on the bone tissue. For example, the feature is a hole in the bone tissue. In this case, the spacer includes a member (e.g., a pin or a tooth) that projects distally from the tissue-engaging portion of the guide for insertion into the hole. The member may be retractable with respect to the tissue-engaging portion, or not. The member may be disposed on a sleeve that is insertable over the guide. If the feature includes a region of cartilage on the bone tissue, the spacer may include an enlarged lip disposed adjacent to the tissue-engaging portion of the guide for engaging the region of cartilage.

In some embodiments, the guide includes a window for allowing viewing of the passage. The guide may include a valve for blocking fluid flow through the passage. In other embodiments, a portion of the guide comprises clear material.

Another aspect of the invention features a set of instruments that includes the guide, the drill, and the insertion tool.

In preferred embodiments, these instruments are sized to insert a tissue graft having a selected size. At least one other set of such instruments may be provided and sized to insert tissue grafts of a different size.

The set of instruments may also include the dilator and a template for measuring a size of the tissue graft.

In addition, the set may include a tool for removing the tissue graft from a bone. The tool includes a chisel having a hollow shaft that extends distally from a handle and terminates in a sharpened, hollow tip configured to capture the tissue graft therein, the handle having a passage therein that communicates with the hollow shaft. A collar is slidable over the shaft to shield the hollow tip during removal of the tissue graft therefrom, and a member is insertable into the hollow tip to engage the tissue graft and remove the tissue graft proximally through the shaft and the passage of the handle. The collar includes a flared opening disposed adjacent to the tip when the collar is inserted over the shaft. The member applies force to the bone portion of the graft—rather than the cartilage on the upper surface of the graft—during removal, thereby reducing the risk of damaging the cartilage.

The set of instruments may also be equipped with a device for determining an entry portal for the guide over the bone surface. The device includes a needle disposed along a longitudinal axis and having an open distal end, and a plurality of prongs disposed within said needle and having resiliently curved distal tips. The prongs are slidable within the needle between a retracted position in which the distal tips are disposed within the needle and an extended position in which the distal tips project from the needle to engage the bone surface and define a plane that is perpendicular to the longitudinal axis. The device is small and can be inserted into the body even multiple times to determine the correct (e.g., perpendicular) entry portal location with a minimum of patient trauma.

Another general aspect of the invention features a method of inserting a tissue graft using the instruments discussed above.

Among other advantages, the invention provides an efficient and accurate way of repairing cartilage that may be performed arthroscopically, thereby reducing trauma and minimizing healing time. The guide allows the graft-receiving holes to formed perpendicularly to the bone surface and the graft to be inserted straight into the hole, despite the curved nature of the bone. This greatly enhances the match between the grafted cartilage and the contour of the surrounding cartilage. In addition, because the height of the graft (i.e., the amount that the graft protrudes from the hole) is adjustable, the grafted cartilage can be easily positioned at the same height as the surrounding cartilage. This provides a high quality repair and reduces the risk that further surgery will be needed to sculpt the grafted cartilage to the height and contour of the surrounding, existing cartilage.

In addition, the various configurations of the guide allow the graft receiving holes to be marked and closely positioned with respect to each other while maintaining sufficient bone wall thickness to promote healing and a healthy environment for the grafts. The accessories provided with the chisel (e.g., the collar and graft-removal member) greatly facilitate withdrawal of the graft from the chisel without injuring the surgeon (with the sharp chisel tip) or damaging the graft (with the graft-removal member). The entry portal positioning device allows the surgeon to determine the correct (e.g., perpendicular) entry portal location with a minimum of patient trauma.

Other features and advantages of the invention will become apparent from the following detailed description, and from the claims.

DRAWINGS

FIGS. 10a and 10b show another embodiment of the guide of FIGS. 2a and 2b.

FIGS. 11a–11c show the guide of FIGS. 2a and 2b with a spacer.

DESCRIPTION

Figure 1:
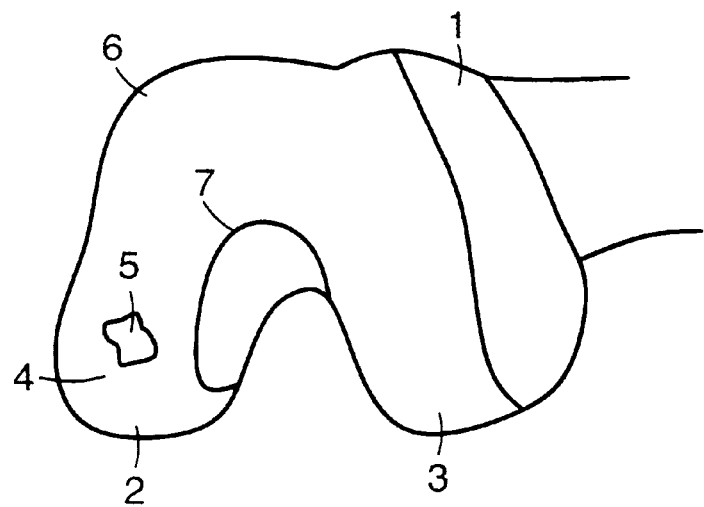
FIG. 1 shows a femur with an area of damaged articular cartilage.

Referring to FIG. 1, this invention features a method for replacing damaged or defective cartilage, e.g., articular cartilage 4 on a patient's femur 1. In addition, the invention provides a set of surgical instruments (described below) for performing the procedure efficiently and accurately.

Articular cartilage 4 covers femoral condyles 2 and 3 and protects them from wear and mechanical shock. Consequently, an area 5 of articular cartilage 4 may become damaged (e.g., torn or excessively worn). The damaged area 5 is repaired by removing the damaged articular cartilage 4 and implanting healthy cartilage harvested from another area of femur 1, such as the ipsilateral side of the nonarticular condylar surface 6 or the intercondylar notch 7.

FIGS. 2a–2f show a set of surgical instruments for repairing damaged area 5 of articular cartilage. The surgical instruments include a guide 12 (FIGS. 2a, 2b), a chisel 20 (FIG. 2c), and a series of instruments—a drill 40 (FIG. 2d), a dilator 47 (FIG. 2e), and an insertion tool 50 (FIG. 2f)—that are used with guide 12 during the procedure. The instruments and the procedure are described in detail below, but briefly, chisel 20 is used to cut a cylindrical bone and cartilage graft from, e.g., the ipsilateral side of the nonarticular condylar surface 6 or the intercondylar notch 7. After the damaged cartilage 4 has been removed in damaged area 5 to expose the condylar bone surface, drill 40 is inserted through guide 12 to drill a hole in the bone that will receive the graft, and dilator 47 is inserted through guide 12 to slightly and temporarily enlarge the hole to accommodate the graft. Finally, the graft is implanted into the hole with insertion tool 50. This procedure is repeated until an array of bone and cartilage grafts have been implanted to fill damaged area 5 with replacement cartilage.

To ensure that the grafted cartilage follows the contour of surrounding cartilage 4, the bone and cartilage grafts must be formed perpendicularly to the bone surface, and the graft-receiving holes must also be drilled perpendicularly to the bone surface. In addition, grafts must be inserted to the proper depth so that the grafted cartilage neither protrudes nor is recessed from the surrounding cartilage. The instruments and surgical technique provided by the present invention achieves these goals.

Figure 2A:
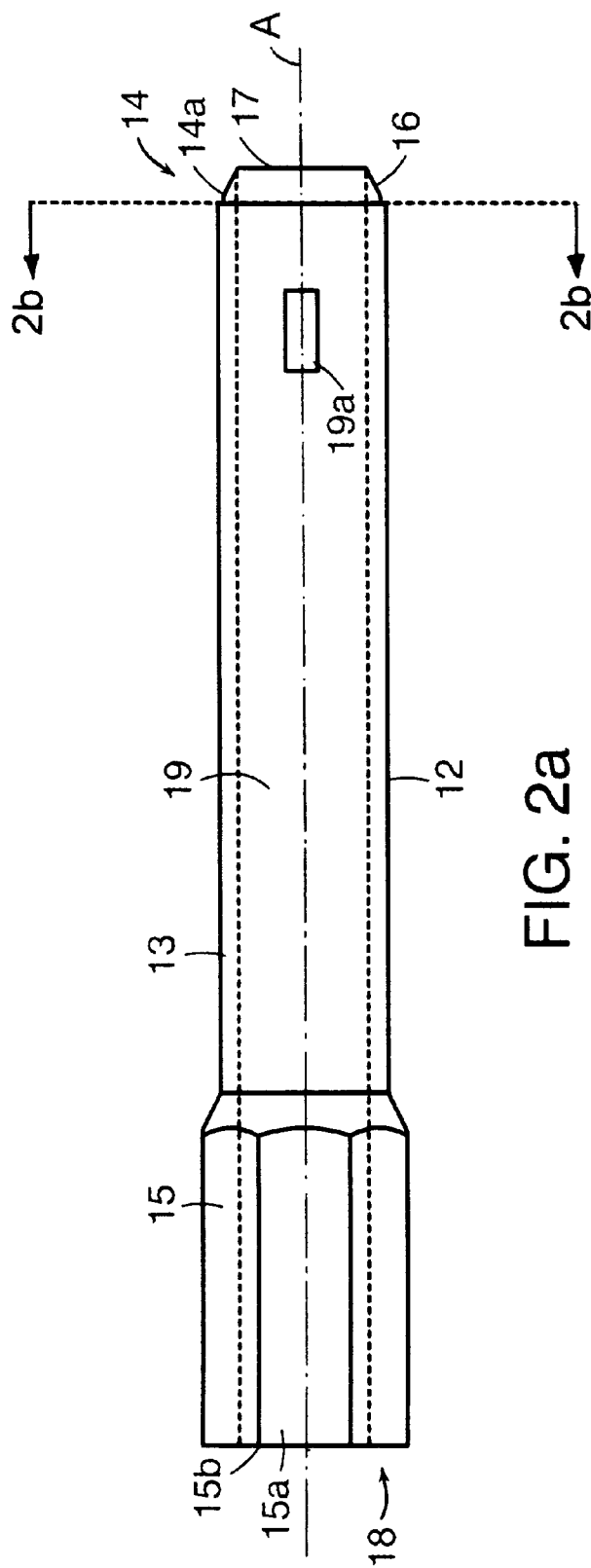
FIGS. 2a–2f show a set of surgical instruments for repairing the area of damaged articular cartilage.
Figure 2B:
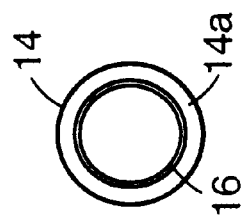

Guide 12 is the device that ensures the perpendicular formation of the graft-receiving holes. Guide 12 includes a hollow tube 13 with an interior passage 19 that extends between open distal and proximal ends 17, 18. Guide 12 is elongated along a longitudinal axis A, and a rim 14a at distal end 17 of tube 13 (FIG. 2b) defines a tissue-engaging portion 14 in a plane A' oriented perpendicularly to axis A. As shown in FIG. 2a, the outer diameter of tube 13 decreases in a step-like manner to form rim 14a and then gradually decreases to form flange 16. Rim 14a has a width of 0.5 mm, and flange 16 has a length of 3 mm from rim 14a to a distal end of flange 16. In addition, the edge of flange 16 is slightly chamfered. Accordingly, when guide 12 is positioned on the bone surface (such as a curved surface on femur 1) so that flange 16 is seated in the bone and rim 14a contacts and is flush with the bone completely around its circumference, axis A is perpendicular to the bone surface. By being seated in the bone, flange 16 helps to hold the perpendicular position of guide 12. Thus, an instrument (e.g., chisel 20 drill 40, dilator 47, or insertion tool 50) inserted through guide passage 19 is aligned perpendicularly to the bone surface.

Passage 19 is sized and shaped to receive drill 40, dilator 47, and insertion tool 50, which in turn are dimensioned according to the desired diameter of the graft (e.g., 2.7 mm, 3.5 mm, 4.5 mm, 6.5 mm or 8.5 mm). Alternatively stated, a complete set of instruments that includes a guide 12, a drill 40, a dilator 47, and an insertion tool 50 (as well as a chisel 20) is provided for each size graft desired to be inserted into defect area 5.

Guide 12 also includes a handle 15 located near proximal end 18. Handle 15 has a larger outer diameter than the remainder of guide 12 and includes a series of flat, faceted surfaces 15a arranged around the circumference of guide 12 for ease of gripping. The diameter of passage 19 is constant over the length of guide 12. As a result, handle 15 provides a thickened rim 15b surrounding open proximal end 18 to withstand the impact of instruments (such as insertion tool 50) during use, as will be described below. A window 19a formed in the walls of tube 13 near distal end 17 is open to passage 19. Window 19a allows the surgeon to see into passage 19 during use to, e.g, visualize the position of the graft Guide 12 has a one-way valve 19b (shown schematically in FIG. 2a) located near proximal end 18 to block fluid flow through passage 19 when an instrument is inserted in (and removed from) guide 12.

Guide 12, tissue-engaging portion 14, and handle 15 are made from metal and may be integrally formed (e.g., by casting) as a single piece of material. Alternatively, guide 12, tissue-engaging portion 14, and handle 15 may be made from molded or extruded plastic. As discussed above, guide 12 is available in various sizes depending on the size of the surgical instrument to be inserted through guide 12.

Chisel 20 (shown in FIG. 2c with auxiliary components 30, 32 that are described below) includes an axially elongated, hollow metal shaft 21 that extends distally from a handle 28 to a distal end 24 that terminates in a sharpened, open chisel tip 22. The interior of chisel tip 22 tapers inwardly at 22a to grasp the sides of the graft removed from femur 1. Chisel 20 is available in various sizes depending on the desired size (e.g., diameter) of the graft. For example, chisel 20 may be sized to cut a bone graft having a diameter of 2.7 mm, 3.5 mm, 4.5 mm, 6.5 mm or 8.5 mm. Chisel 20 is described in German Patent No. DE 19503504 A1 and Hungarian Patent No. HU 9402663 A0, each of which is incorporated herein by reference.

Handle 28 includes an axial passage that communicates with the interior of shaft 21 and is open at the proximal end of handle 28 for purposes to be described. A transverse hole 26 formed through handle 28 near its proximal end receives the shaft 31 of a tamp 32 during use. That is, tamp 32 is inserted transversely through handle 28 to provide the surgeon with increased leverage when chiseling a graft (see FIG. 4). Tamp 32 serves the additional purpose of removing the graft from chisel 20. A chisel guard 30 is also provided and is insertable over shaft 21 to help avoid injury from chisel tip 22 while the graft is being removed. Chisel guard 30 is a hollow cylinder that includes an enlarged head 33 with a flared opening 33a positioned adjacent to chisel tip 22 when guard 30 is inserted over shaft 21. Flared opening 33a allows the surgeon to insert tamp 32 easily into chisel tip 22. Chisel guard 30 is approximately as long as chisel shaft 21 and is available in various sizes depending on the size of chisel 20.

To remove the graft from chisel 20, chisel guard 30 is inserted over shaft 21 so that it abuts handle 28. With chisel tip 22 shielded by guard 30, the surgeon inserts tamp shaft 31 into chisel tip 22 to engage the underside of the bone graft, and pushes the graft proximally from tip 22 and out of handle 28. As a result, the force applied to remove the graft from chisel 20 is applied to the bone portion of the graft, rather than to the cartilage on the upper surface of the graft. This helps reduce the risk of tearing or otherwise damaging the grafted cartilage.

Drill 40 (FIG. 2d) includes an axially elongated metal shaft 41 that fits through guide passage 19 and terminates in a drill bit 42 at distal end 44. Drill shaft 41 has graduated markings 41a, 41b near its proximal and distal ends so that the surgeon can see the position of drill 40 when inserted through guide 12. For example, the surgeon can see distal markings 41b through window 19a of guide 12. Drill bit 42 includes a pointed distal tip 43a and a plurality of cutting flutes 43b circumferentially spaced around drill bit 42 proximally adjacent to tip 43a. The pointed nature of tip 43a helps prevent drill bit 42 from "walking" on the bone surface so that the graft-receiving holes can be positioned more accurately. Drill 40 is available in various sizes depending on the size of the bone graft. For example, drill 40 may be sized to cut a hole having a diameter slightly smaller than 2.7 mm, 3.5 mm, 4.5 mm, 6.5 mm or 8.5 mm.

Dilator 47 (FIG. 2e) is used to slightly enlarge the hole formed by drill 40, e.g., by about 0.2 mm, to accommodate the graft cut by chisel 20. Dilator 47 is a solid metal rod 46 that is axially elongated between proximal and distal ends 49a, 49b. The diameter at distal end 49b corresponds to the diameter of drill 40 with which dilator 47 is used. The edge of distal end 49b is slightly chamfered (not shown) to allow dilator 47 to be easily inserted into the hole. Moving proximally from distal end 49b, the diameter of dilator 47 gradually increases by 0.2 mm over a distance D of 15 mm (e.g., to a final diameter of 4.7 mm from a distal end diameter of 4.5 mm). Rod 46 has graduated markings 46a, 46b near its proximal and distal ends, so that the surgeon can see the position of dilator 47 when inserted through guide 12. A transverse hole 48 is provided near proximal end 49a and is sized to receive a tamp 32 (FIG. 2c) to form a "T" shaped assembly that provides the surgeon with increased leverage when using dilator 47 to enlarge the graft-receiving hole.

Insertion tool 50 (FIG. 2f) includes an axially elongated cylindrical metal rod 60 the proximal end 62 of which is received within a chamber 72 in a handle 70 to allow the length L of rod 60 that protrudes from the distal end 71 of handle 70 to be adjusted. The proximal end 73 of handle 70 has an enlarged shape to enable the surgeon to securely grasp handle 70 while adjusting length L.

Rod 60 is sized to fit within guide passage 19 and has a flat distal end 64 oriented perpendicularly to rod axis B. The proximal portion 62 of rod 60 has a threaded portion 66 which corresponds with a threaded portion 74 of handle 70. Calibration markings 69 are disposed on rod 60 distal of proximal portion 62. Markings 69 are spaced 1 mm apart and may be designated by numerals (0, 1, 2, etc.).

The configuration of chamber 72 is substantially complementary to that of the portion of rod 60 that fits within handle 70. That is, chamber 72 includes a threaded portion 74 which receives threaded portion 66 of rod 60. An O-ring 76 is disposed in a groove 75 formed around the exterior of chamber 72 slightly proximally of handle end 71.

The surgeon adjusts the length L of rod 60 by rotating rod 60 with respect to handle 70 (e.g., by twisting rod 60 further into handle 70) while observing calibration markings 69. The friction between O-ring 76 and rod 60 helps to hold rod 60 in place within handle 70 at the position set by the surgeon. Markings 69 indicate the length of rod 60 protruding from handle 70, and more specifically identify the spacing between rod distal end 64 and tissue-engaging portion 14 of guide 12 (FIG. 2a). For example, when marking 69 designated by numeral 0 is aligned with handle distal end 71, the length L of rod 60 equals that of guide 12 to rim 14a, and as a result rod distal end 64 is flush with rim 14a when insertion tool 50 is fully inserted into guide 12 (with distal end 71 of handle 70 abutting guide proximal end 18).

Inserting rod 60 farther into handle 70 causes rod distal end 64 to be recessed from rim 14a by a distance that corresponds to the calibration marking 69 (e.g., 1 mm, 2 mm, 3 mm, etc.) that is aligned with handle distal end 71. For example, when length L of rod 60 is set at the marking designated by the numeral 3, distal end 64 of rod 60 is recessed by 3 mm from rim 14a of guide 12. This enables the surgeon to insert the graft at a precise depth in the graft receiving hole so that the cartilage on the graft protrudes from the hole by an amount that corresponds to the height of the surrounding cartilage 4 (FIG. 1).

As discussed above with respect to FIG. 1, damaged articular cartilage 4 from area 5 is repaired by removing damaged cartilage 4 and implanting grafts with healthy cartilage harvested from elsewhere on femur 1. The use of the instruments shown in FIGS. 2a–2f in the grafting procedure will now be described with reference to FIGS. 3–9.

Figure 3:
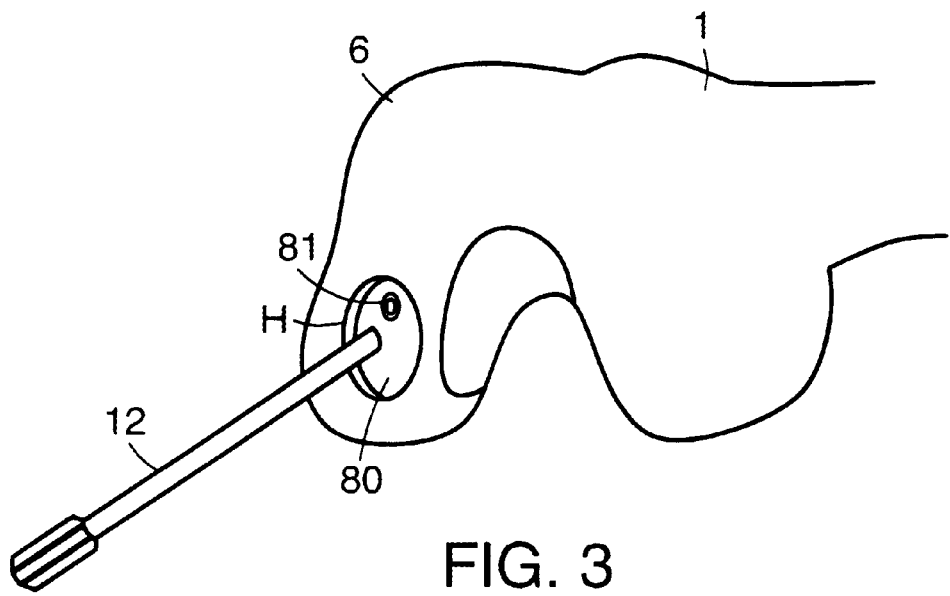
FIGS. 3–9 show the use of the instruments shown in FIGS. 2a–2f in repairing the area of damaged articular cartilage.

Referring to FIG. 3, the first step is to remove cartilage in damaged area 5 and immediately surrounding areas to create an area 80 of exposed bone surface. The depth H of exposed area 80 is measured to determine the thickness of articular cartilage 4 surrounding exposed area 80. Guide 12 is used to determine the optimal number and size of grafts to be implanted into exposed area 80. As shown in FIG. 3, this is done by using guide 12 (FIGS. 2a, 2b) to mark hole locations 81 in exposed area 80. When guide 12 is tapped into exposed area 80, rim 14a of guide 12 forms hole location 81 by leaving an annular impression (defined by flange 16 and the exterior edge of rim 14a) in exposed area 80. The holes should be located close together so that a tightly-packed matrix of healthy grafted cartilage can be implanted to cover area 80 as completely as possible. But a sufficient wall thickness (e.g., 1 mm) should be maintained between adjacent holes to provide a stable and healthy environment for the implanted grafts. Rim 14a of guide 12 helps to maintain sufficient wall thickness between holes. As discussed above, rim 14a has a width of 0.5 mm. Thus, when guide 12 is used to mark hole locations 81, adjacent hole locations 81 have a wall thickness of at least 1 mm.

Figure 2C:
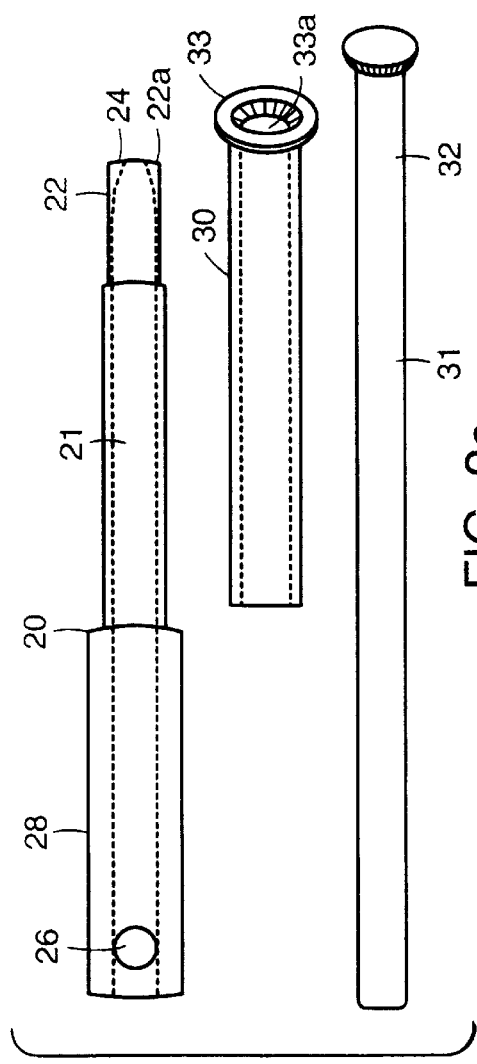
Figure 2D:
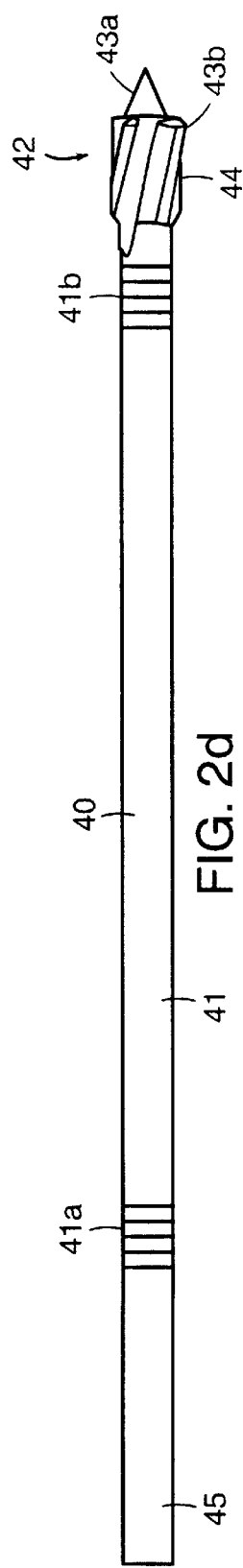
Figure 2E:
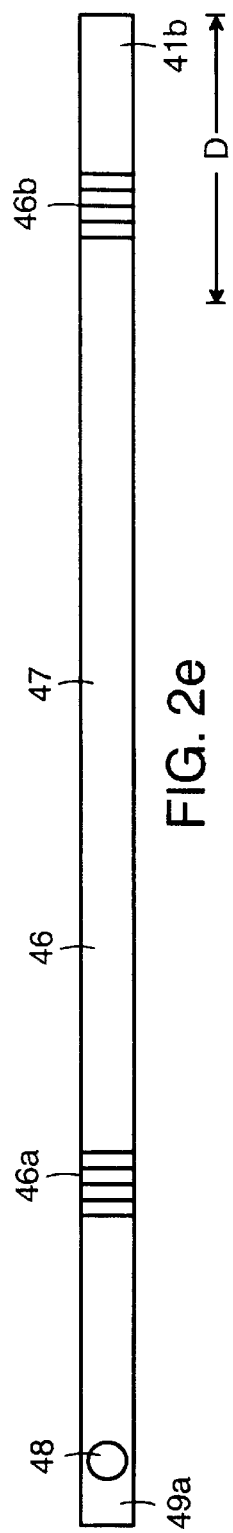
Figure 2F:
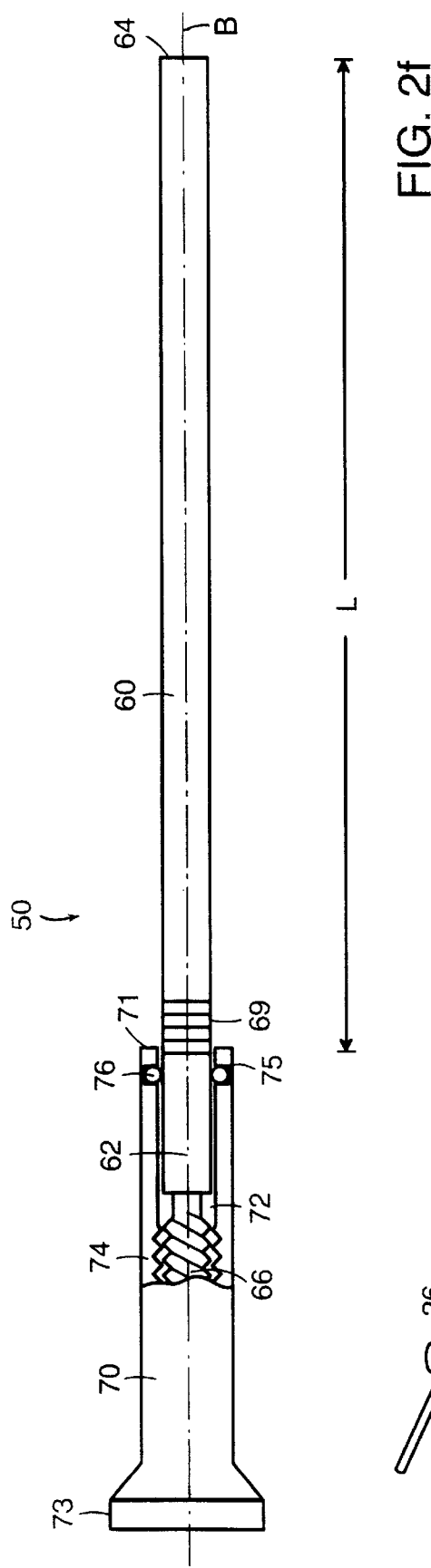
Figure 4:
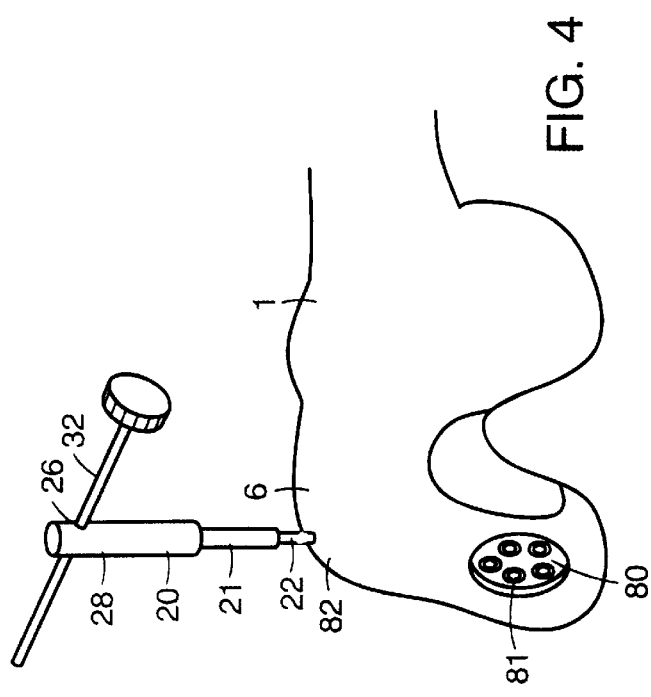

Referring to FIG. 4, after marking hole locations 81 in exposed area 80, healthy cartilage is harvested from a donor site 82 located, e.g., at the ipsilateral side of the nonarticular condylar surface 6 of femur 1 using chisel 20 (FIG. 2c). Chisel 20 is inserted into the patient's body so that chisel tip 22 engages the surface of donor site 82. The surgeon gently rocks chisel 20 back and forth on the surface of cartilage 4 until he feels that chisel tip 22 is flush with the surface. With chisel tip 22 in this orientation, chisel shaft 21 is perpendicular to the cartilage surface at donor site 82.

With chisel 20 aligned perpendicularly to the surface of donor site 82, the surgeon taps or pounds chisel handle 28 with a hammer (not shown) to drive chisel tip 22 into the bone beneath donor site 82 to a depth of 15 mm–20 mm. After chisel 20 is fully seated, the surgeon inserts tamp 32 through hole 26 of chisel handle 28 to form a "T" shaped tool, which the surgeon moves back and forth until the graft breaks away from the underlying bone. Chisel 20 is then pulled straight up and out of the patient's body. The tapered interior 22a of chisel tip 22 holds the graft within tip 22 as the instrument is withdrawn.

Figure 5A:
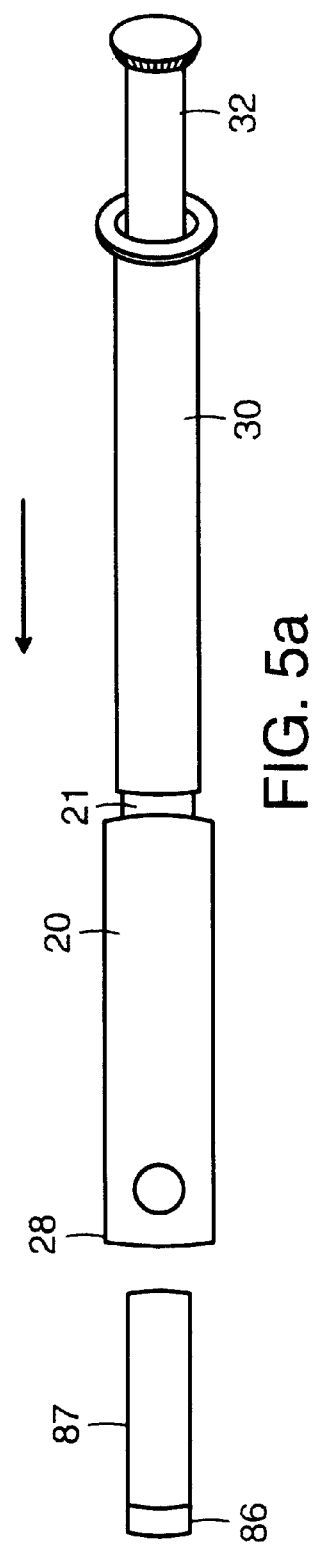

Referring also to FIG. 5a, graft 87 is primarily bone tissue the proximal end of which is covered by a layer of hyaline cartilage 86. Graft 87 is removed from chisel 20 by sliding chisel guard 30 over chisel tip 22, inserting tamp 32 into chisel distal end 24, and pushing against the bony distal end of graft 87 to slide graft 87 through chisel shaft 21 and out of the proximal end of handle 28. Removing graft 87 in this manner avoids the need to push against hyaline cartilage 86 (i.e., as would be done by inserting tamp 32 into handle 28 rather than into tip 22), thereby reducing the risk of damaging hyaline cartilage 86. This is particularly important because graft 87 often is tightly wedged within tip 22 due to the large forces applied during chiseling. After graft 87 is removed from chisel 20, graft 87 may be cut to the desired length (e.g. 15 mm).

Figure 5B:
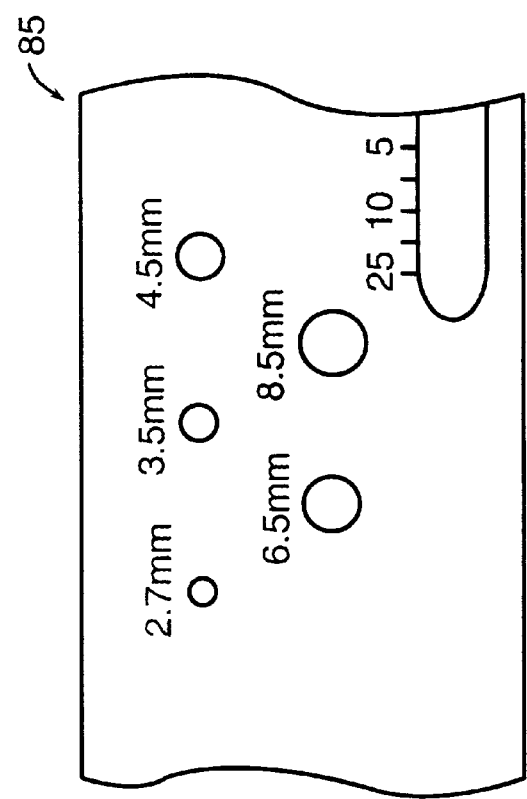

Referring also to FIG. 5b, a measuring template 85 may be used to determine the length and outer diameter of harvested bone graft 87. The desired size of graft 87 will vary depending on the condition of the harvested graft 87 (e.g., cracks or chips in the graft) and the age of the patient. The size of bone graft 87 as indicated by template 85 will provide an indication to the surgeon as to how much (if at all) a graft-receiving hole should be temporarily enlarged with dilator 47. After harvesting a preselected number of grafts 87 from donor site 82 (or other donor sites on femur 1 or elsewhere), the incisions made over donor site 82 are closed and sutured. Alternatively, grafts 87 can be removed from donor site 82 and implanted in exposed area 80 one at a time.

Figure 6:
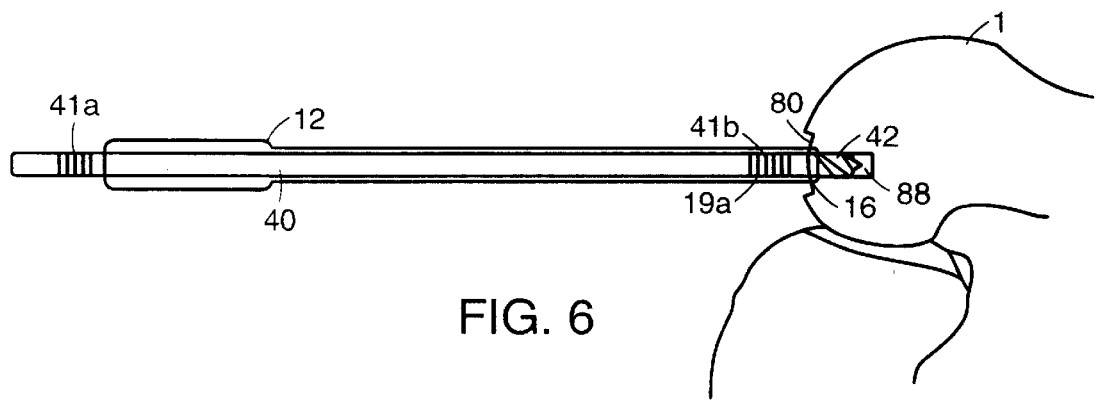

Referring to FIG. 6, the first step in the graft implantation portion of the procedure is to insert guide 12 into the patient's body so that rim 14a is centered over one of hole locations 81 in exposed area 80. The surgeon seats flange 16 into the bone and rocks guide 12 back and forth until he feels that rim 14a is flush against exposed area 80, thereby indicating to the surgeon that passage 19 is aligned perpendicularly to the curved bone surface at hole location 81. While holding guide 12 firmly in the perpendicular orientation, the surgeon inserts drill 40 through guide 12 and drills a graft-receiving hole 88 in area 80. Because of the alignment provided by guide 12, hole 88 is formed perpendicularly to the bone surface. By observing markings 41a near proximal end of drill 40 outside the patient's body and markings 41b near distal end of drill 40 through window 19a, the surgeon can limit the depth of hole 88 to, e.g., 15 mm. Drill 40 is then removed from guide 12 and the patient, but the position of guide 12 is maintained.

Figure 7:
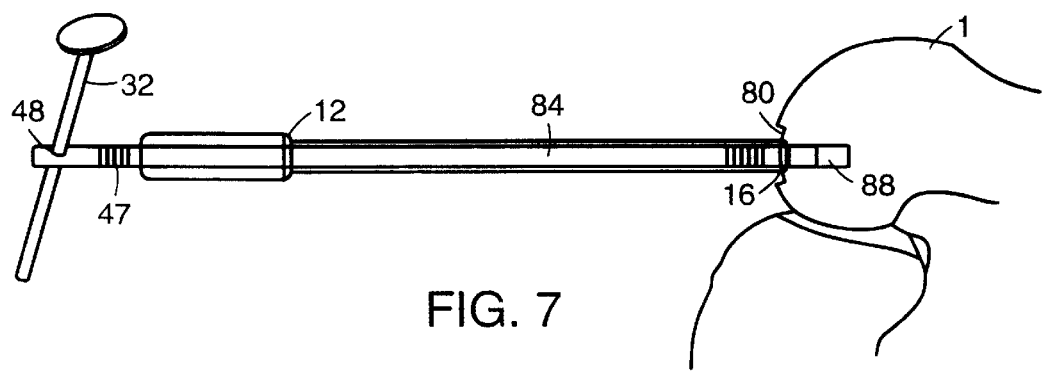

As shown in FIG. 7, dilator 47 is inserted through guide 12 and into hole 88 to slightly (e.g., by 0.2 mm) and temporarily enlarge hole 88 so that it will more readily receive graft 87. (Hole 88 relaxes to its original size shortly after graft 87 is inserted to securely grip graft 87 for proper healing.) This operation is facilitated by inserting tamp 32 through hole 48 near the proximal end of dilator 47 to form a "T" shaped tool that is used in much the same way as described above for chisel 20. Dilator 47 is then removed, but again, guide 12 is left in place over hole 88.

Figure 8:
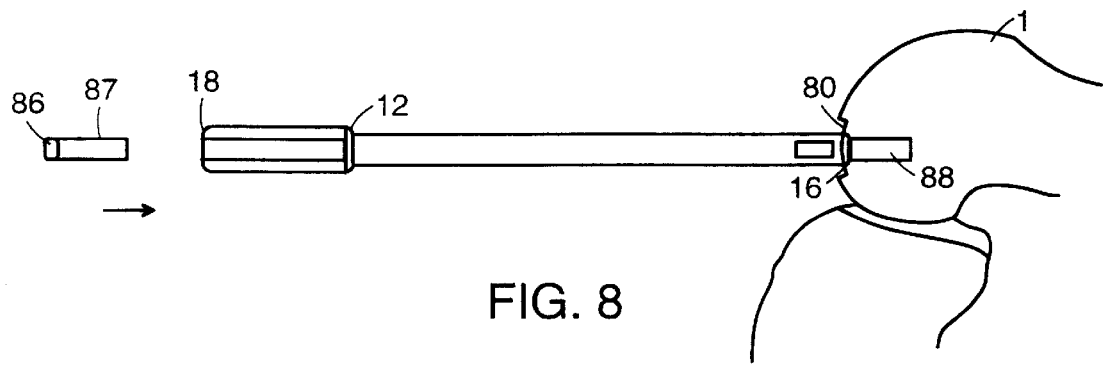

Referring to FIG. 8, graft 87 is inserted into proximal end 18 of guide 12 with layer of hyaline cartilage 86 facing proximal end 18. The surgeon then adjusts length L of rod 60 (FIG. 2f) based on the measured depth H of exposed area 80 to set the height at which cartilage layer 86 will protrude from the bone surface. For example, if exposed area 80 has a depth H of 2 mm, then length L is adjusted to align calibration mark "2" with handle distal end 71, thereby providing a 2 mm recess between rod distal end 64 and rim 14a of guide 12 when insertion tool 50 is fully inserted into guide 12.

Figure 9:
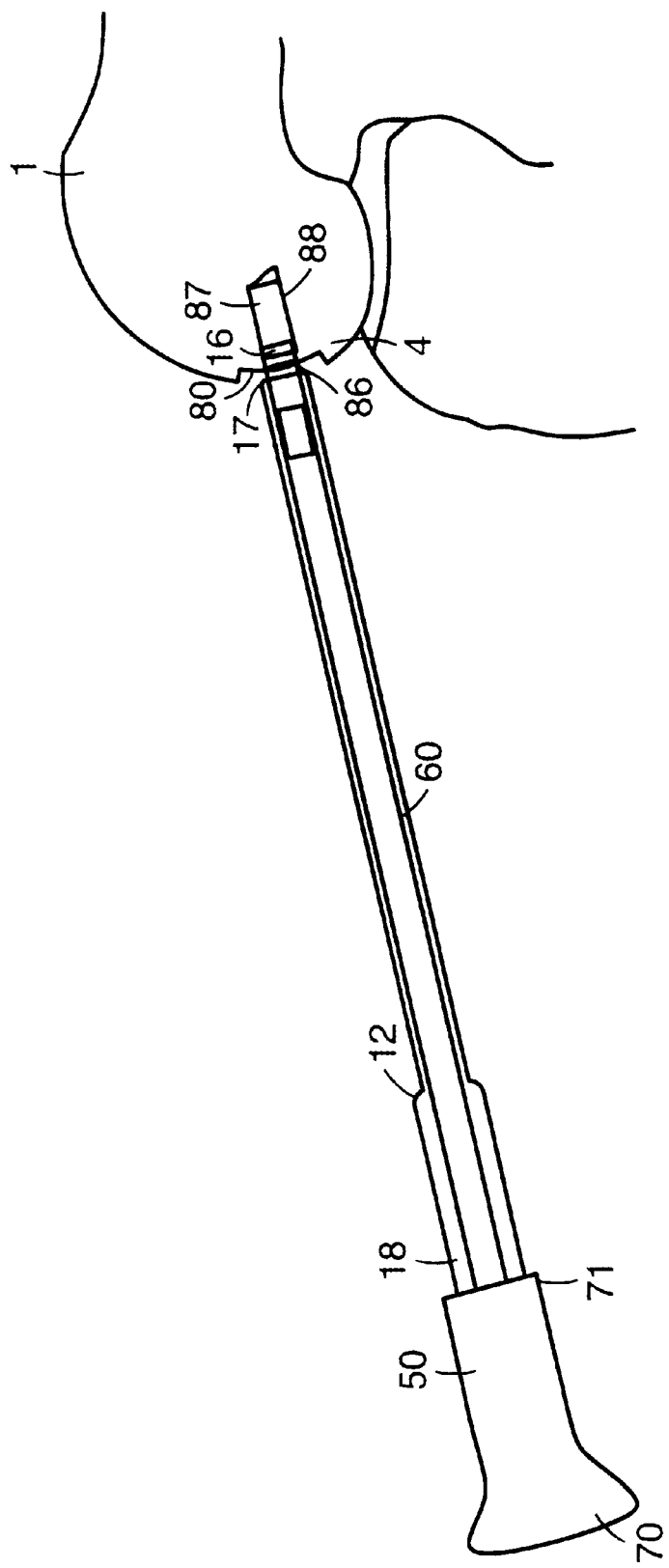

As shown in FIG. 9, graft 87 is implanted at the desired depth in hole 88 by advancing insertion tool 50 into guide 12 until distal end 71 of handle 70 abuts proximal end 18 of guide 12. Thus, rod 60 pushes graft 87 out of distal end 17 of guide 12 and positions graft 87 at the desired depth in hole 88 such that the layer of hyaline cartilage 86 on graft 87 is flush with the layer of articular cartilage 4 surrounding exposed area 80. This process is repeated until all the harvested grafts 87 are implanted into exposed area 80.

As exposed area 80 becomes filled with implanted grafts 87, it may be necessary to adjust the length L of insertion tool rod 60 so that the later-inserted grafts are implanted to the proper depth. For example, if rim 14*a* of guide 12 rests on implanted grafts 87 rather than exposed bone in area 80, rod length L must be increased to reduce the recess between rod distal end 64 and rim 14*a* of guide 12.

Other embodiments are within the scope of the following claims.

For example, the guide may have configurations other than tubular. The guide may be a solid member with an exterior channel for receiving the drill, insertion tool, etc. Alternatively, the guide may include a post to which a series of axially spaced, aligned rings are attached for receiving the other instruments.

Referring to FIGS. 10*a* and 10*b*, guide 90 has a tissue-engaging portion in the form of an enlarged lip 89 that defines a plane A' perpendicular to the axis A of guide 90. Lip 89 has a slightly concave surface (e.g., with a radius of curvature of 1 inch) and extends outwardly from guide 90 (e.g., by 0.5 mm). A portion of lip 89 may be removed to define a recess 91 having a curvature that approximates the contour of graft 87. Recess 91 enables lip 89 to be positioned more closely to previously inserted grafts 87 or other structures in area 80 (such as cartilage 4 surrounding exposed area 80).

Referring to FIGS. 11*a*–11*c*, the guide may include various spacers for positioning the guide in a lateral orientation with respect to previously inserted grafts 87 or other structures in area 80. FIG. 11*a* shows a spacer 92 that has a pin shape and is located along a side of the guide. Spacer 92 may be retractable, or not.

The spacer may have other configurations. For example, spacer 94 (FIG. 11*b*) has a tooth shape. Spacer 96 (FIG. 11*c*) is in the form of an enlarged rim portion and provides the spacing by being engaged against the side of a previously inserted graft 87 or, alternatively, by being aligned with the side of an adjacent hole 88.

Figure 12A:
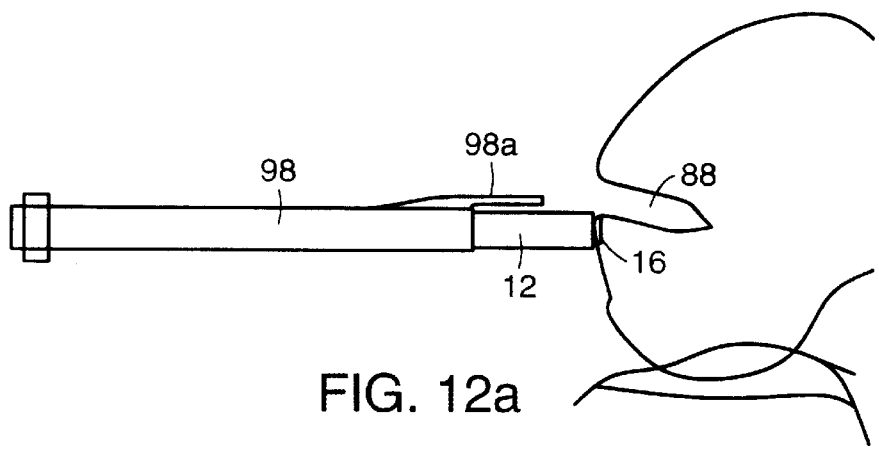
FIGS. 12a and 12b show the use of the guide of FIGS. 2a and 2b with a retractable spacer.
Figure 12B:
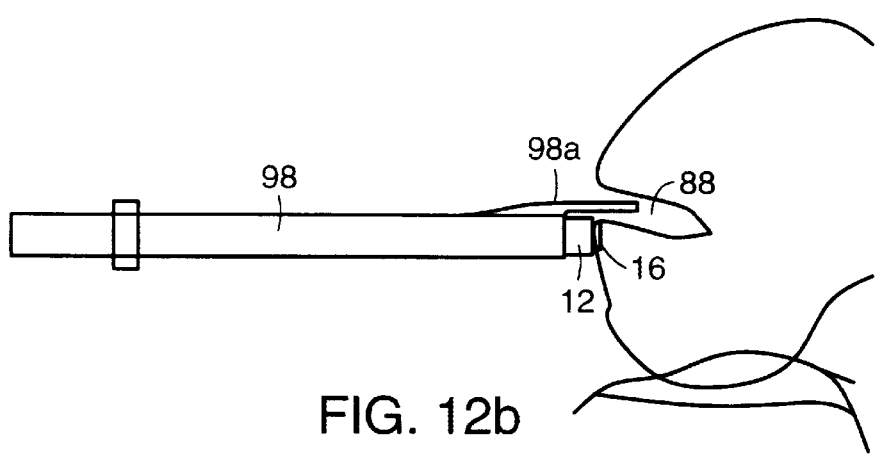

As shown in FIGS. 12*a* and 12*b*, another embodiment of a retractable spacer includes a sleeve 98 with a projecting pin 98*a* inserted over guide 12. Pin 98*a* enters a previously-formed graft receiving hole 88 to position guide passage 19 a selected distance therefrom. This feature helps provide sufficient bone wall thickness between adjacent holes 88.

Figure 13A:
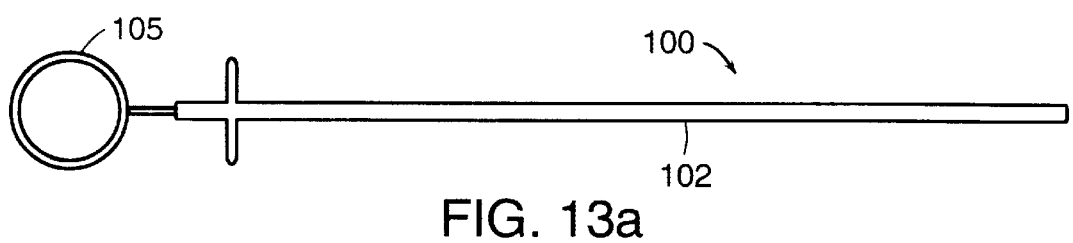
FIGS. 13a and 13b show another guide for locating perpendicularity with respect to a tissue surface.
Figure 13B:
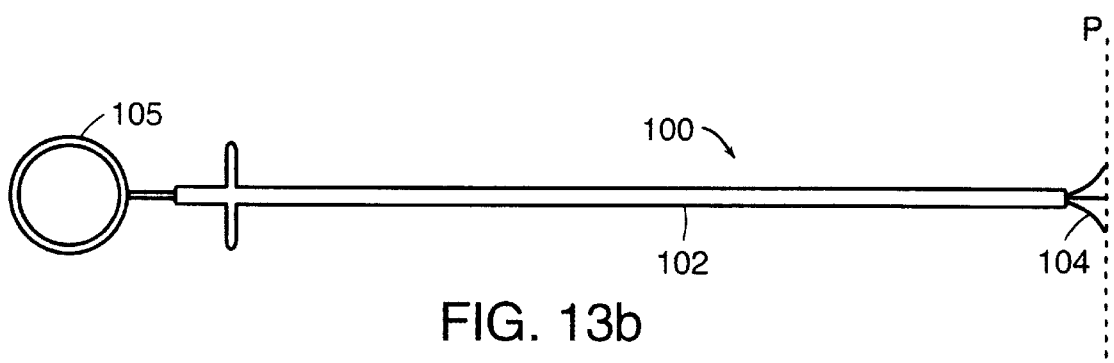

Referring to FIGS. 13*a* and 13*b*, guide 100 includes a hypodermic needle 102 within which a set of retractable wire prongs 104 are disposed. The distal end of each prong 104 is resiliently biased outwardly so that when prongs 104 are extended the tips of prongs 104 define a plane P oriented perpendicular to needle 102. The proximal ends of prongs 104 are connected to a handle 105, which is slid within needle 102 to selectively retract and extend prongs 104. Guide 100 is used, for example, to approximate the perpendicular approach to the bone before making an incision in the tissue. Thus, guide 100 may be used to determine the entry location for guide 12.

Figure 14A:
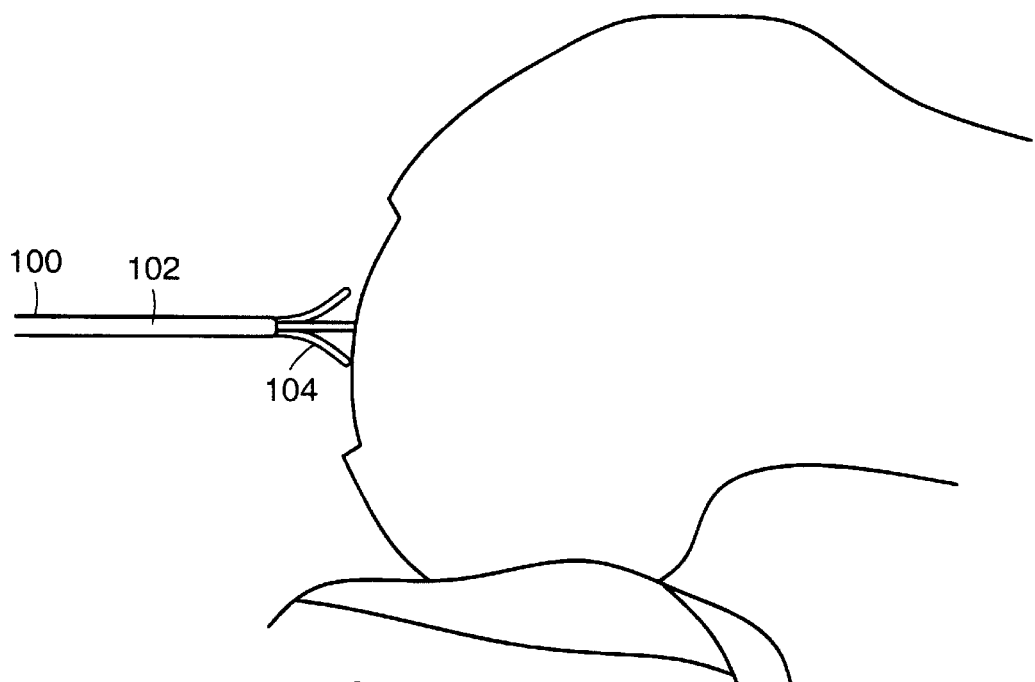
FIGS. 14a and 14b show the use of the guide of FIGS. 13a and 13b in locating perpendicularity with respect to a tissue surface.
Figure 14B:
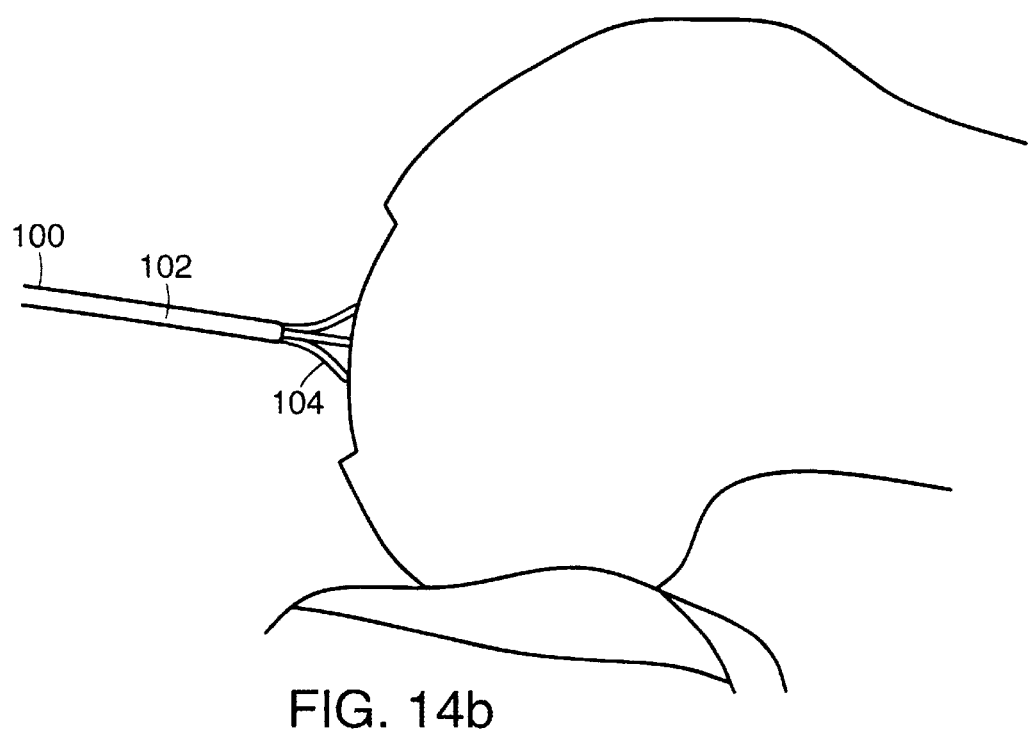

As shown in FIGS. 14*a* and 14*b*, after needle 102 is inserted into the patient's body, prongs 104 are extended from the tip of needle 102. If one or more prongs 104 do not engage the bone surface, then prongs 104 are retracted into needle 102, and needle 102 is withdrawn from the patient's body. Needle 102 is then reinserted into the patient's body in another area to locate perpendicularity with respect to the bone surface. If all prongs 104 engage the bone surface, needle 102 is perpendicular to the bone surface.

In other embodiments, guide 12 may have a one-way valve 93 (shown schematically in FIG. 10*a*) located near proximal end 18 to block fluid flow through passage 19 from window 19*a* when an instrument is inserted in (and removed from) guide 12. Alternatively, window 19*a* may be formed of clear plastic and thus, closed to passage 19. In still other embodiments, tube 13 may be made from clear plastic, thereby obviating the need for window 19*a*.

The length of rod 60 may be adjusted in other ways, such as by simply sliding rod 60 axially toward and away from handle 70. Insertion tool 50 may be made partially or wholly from plastic. A button of plastic or a soft material may be attached to distal tip 64 to protect the cartilage on the upper surface of graft 87 from damaged during insertion. With respect to drill 40 or dilator 47, a stop may be provided at its proximal end to engage guide proximal end 15*b* and limit the extent to which drill 40 or dilator 47 can be advanced into the bone. The stop may be adjustable, or not.

There has been described novel and improved apparatus and methods for replacing damaged or defective cartilage with grafts harvested from elsewhere in the body. Although the invention has been describe in inserting the grafts into pre-drilled holes in the femur, the invention may be used with other tissue surfaces and in other areas of the body, such as the ankle, hip, and shoulder. It is evident that those skilled in the art may now make numerous uses and modifications of and departures from the specific embodiments described herein without departing from the inventive concept.

What is claimed is:

1. A set of instruments for use during a procedure in which a tissue graft is inserted into bone tissue, the set of instruments comprising a first instrument; and a second instrument, wherein:

the first instrument is configured to orient the second instrument against a surface of the bone tissue, said first instrument including a guiding portion disposed along a longitudinal axis for engaging the second instrument, a tissue-engaging portion, and at least one viewing portion permitting visual inspection of an interior of the guiding portion through a side wall of the guiding portion; and said second instrument is confined for inserting the tissue graft into a hole in the bone tissue, said guiding portion being sized to engage and align a portion of said second instrument against the bone tissue surface.

2. The set of instruments of claim 1 further comprising a drill for drilling a hole in the bone tissue surface for receiving the tissue graft, said guiding portion being sized to engage and align said drill perpendicularly to the bone surface.

3. The set of instruments of claim 2 wherein said drill includes a distal end that comprises a pointed distal tip and a plurality of cutting flutes circumferentially spaced around said distal end proximally adjacent to said tip.

4. The set of instruments of claim 2 wherein said drill includes markings to indicate a depth of the hole.

5. The set of instruments of claim 2 further comprising a dilator having a distal end sized to enlarge the hole, said guiding portion being sized to engage and align said dilator perpendicularly to the bone surface.

6. The set of instruments of claim 5 wherein said distal end of said dilator is tapered.

7. The set of instruments of claim 5 wherein said dilator includes markings to indicate a depth that said distal end is inserted in the hole.

8. The set of instruments of claim 1 wherein said portion of said second instrument includes a rod attached to a handle that is configured to engage a proximal end of said first instrument, said rod having an adjustable length relative to said handle.

9. The set of instruments of claim 8 wherein said rod has a distal end configured to engage the graft and a proximal end that is progressively insertable into an opening in said handle to adjust the length of said rod relative to said handle.

10. The set of instruments of claim 9 wherein said proximal end of said rod is threadably received within said opening to allow adjustment of said length by relative rotation between said handle and said rod.

11. The set of instruments of claim 9 further comprising a resilient member disposed in said opening in engagement with said proximal end of said rod for maintaining said rod in position at the adjusted length.

12. The set of instruments of claim 8 wherein said rod includes markings to indicate the amount by which the graft protrudes from the hole.

13. The set of instruments of claim 1 wherein said first instruments comprises a tube having a passage disposed along said longitudinal axis to provide said guiding portion, said tissue-engaging portion being disposed at a distal end of said tube.

14. The set of instruments of claim 13 wherein said tissue-engaging portion comprises a rim of said tube at said distal end.

15. The set of instruments of claim 14 wherein said tissue engaging portion further comprises an annular flange that projects distally from said rim and is configured to be seated within the bone tissue.

16. The set of instruments of claim 13 wherein said guide includes a window disposed on a side of the tube for allowing viewing of the passage.

17. The set of instruments of claim 16 wherein said guide includes a valve for blocking fluid flow through the passage.

18. The set of instruments of claim 13 wherein a portion of said guide comprises clear material.

19. The set of instruments of claim 1 wherein the tissue graft includes bone having a layer cartilage thereon.

20. The set of instruments of claim 1, wherein said viewing portion in the guiding portion allows visualization of the graft in the guiding portion.

21. The set of instruments of claim 1, wherein said viewing portion comprises a window.

22. The set of instruments of claim 1, wherein said viewing portion comprises a clear material.

23. The set of instruments of claim 1, wherein a portion of said guiding portion comprises a clear material.

24. The set of instruments of claim 1, wherein said portion of said second instrument is adjustable relative to a length of said first instrument to control a position at which the graft is located in the hole.

25. The set of instruments of claim 1, wherein the first instrument is configured to orient the second instrument perpendicularly to the surface of the bone tissue.

26. The set of instruments of claim 1, wherein the tissue engaging portion is oriented perpendicularly to said longitudinal axis.

27. Apparatus for use with an instrument during a procedure in which a tissue graft is inserted into bone tissue, the apparatus comprising a guide configured to orient the instrument against a surface of the bone tissue, said guide including a guiding portion disposed along a longitudinal axis for engaging the instrument, a tissue-engaging portion, and at least one viewing portion permitting visual inspection of an interior of the guiding portion through a side wall of the guiding portion;

wherein said guide further comprises a spacer for positioning said guiding portion at a selected location relative to a feature on bone tissue, said spacer including a member projecting from said tissue-engaging portion of said guide.

28. The apparatus of claim 27, wherein said guide is configured to orient the instrument perpendicularly to the surface of the bone tissue.

29. The apparatus of claim 28 wherein the feature is a hole in the bone tissue and said member projects distally from said tissue-engaging portion of said guide for insertion into the hole.

30. The apparatus of claim 29 wherein said member is retractable with respect to said tissue-engaging portion of said guide.

31. The apparatus of claim 29 wherein said member includes a pin.

32. The apparatus of claim 29 wherein said member includes a tooth.

33. The apparatus of claim 29 wherein said member is disposed on a sleeve that is insertable over said guide.

34. The apparatus of claim 27 wherein said member projects from and is disposed adjacent to said tissue-engaging portion of said guide.

35. The apparatus of claim 27, wherein said member comprises an enlarged lip including a recess.

36. The set of instrunent of claim 27, wherein said viewing portion in the guiding portion allows visualization of the graft in the guiding portion.

37. The set of instruments of claim 27, wherein said viewing portion comprises a window.

38. The set of instruments of claim 27, wherein said viewing portion comprises a clear material.

39. The set of instruments of claim 27, wherein a portion of said guiding portion comprises a clear material.

40. The apparatus of claim 27, wherein said tissue-engaging portion is oriented perpendicularly to said longitudinal axis.

41. A set of instruments for use during a procedure in which a tissue graft that includes bone having a layer of cartilage thereon is inserted into bone tissue, the set of instruments comprising a guide configured to orient another instrument in said set against a surface of the bone tissue, said guide including a guiding portion disposed along a longitudinal axis for engaging said other instrument, a tissue-engaging portion, and at least one viewing portion permitting visual inspection of an interior of the guiding portion through a side wall of the guiding portion, a drill engageable with said guiding portion for drilling a hole in the bone tissue surface for receiving the tissue graft, and an insertion tool engageable with said guiding portion for inserting the tissue graft into the hole formed by said drill, wherein said insertion tool includes a portion having a length that is movable relative to a length of said guide to control a position at which the tissue graft is located in the hole.

42. The set of instruments of claim 41 sized to insert a tissue graft having a selected size, and further comprising at least one other set of said instruments sized to insert a tissue graft having a different selected size.

43. The set of instruments of claim 41 further comprising a dilator engageable with said guiding portion and having a distal end sized to enlarge the hole formed by said drill prior to insertion of the tissue graft.

44. The set of instruments of claim 41 further comprising a tool for removing the tissue graft from a bone.

45. The set of instruments of claim 41 further comprising a template for measuring a size of the tissue graft.

46. The set of instruments of claim 41 further comprising a device for determining an entry portal for said guide over the bone surface, said device comprising a needle disposed along a longitudinal axis and having an open distal end, and a plurality of prongs disposed within said needle and having resiliently curved distal tips, said prongs being slidable within said needle between a retracted position in which said distal tips are disposed within said needle and an extended position in which said distal tips project from said needle to engage the bone surface and define a plane that is perpendicular to said longitudinal axis.

47. The set of instruments of claim 41, wherein said guide is configured to orient another instrument in said set perpendicularly to the surface of the bone tissue.

48. The set of instruments of claim 41, wherein said tissue-engaging portion is oriented perpendicularly to said longitudinal axis.

49. The set of instruments of claim 41, wherein said viewing portion in the guiding portion allows visualization of the graft in the guiding portion.

50. The set of instruments of claim 41, wherein said viewing portion comprises a window.

51. The set of instruments of claim 41, wherein said viewing portion comprises a clear material.

52. The set of instruments of claim 41, wherein a portion of said guiding portion comprises a clear material.

53. A set of instruments for use during a procedure in which a tissue graft that includes bone having a layer of cartilage thereon is inserted into bone tissue, comprising a guide configured to orient another instrument in said set against a surface of the bone tissue, said guide including a guiding portion disposed along a longitudinal axis for engaging said other instrument and a tissue-engaging portion, a drill engageable with said guiding portion for drilling a hole in the bone tissue surface for receiving the tissue graft, an insertion tool engageable with said guiding portion for inserting the tissue graft into the hole formed by said drill, and a tool for removing the tissue graft from a bone, wherein said tool includes a chisel having a hollow shaft that extends distally from a handle and terminates in a sharpened, hollow tip configured to capture the tissue graft therein, said handle having a passage therein that communicates with said hollow shaft, a collar that is slidable over said shaft to shield said hollow tip during removal of the tissue graft therefrom, and a member insertable into said hollow tip to engage the tissue graft and remove the tissue graft proximally through said shaft and said passage of said handle.

54. The set of instruments of claim 53 wherein said collar includes a flared opening disposed adjacent to said tip when said collar is inserted over said shaft.

55. The set of instruments of claim 53, wherein said guide is configured to orient another instrument in said set perpendicularly to the surface of the bone tissue.

56. The set of instruments of claim 53, wherein said tissue-engaging portion is oriented perpendicularly to said longitudinal axis.

57. The set of instruments of claim 53, wherein the guiding portion includes at least one viewing portion permitting visual inspection of an, interior of the guiding portion.

58. The set of instruments of claim 57, wherein said viewing portion in the guiding portion allows visualization of the graft in the guiding portion.

59. The set of instruments of claim 57, wherein said viewing portion comprises a window.

60. The set of instruments of claim 57, wherein said viewing portion comprises a clear material.

61. The set of instruments of claim 53, wherein a portion of said guiding portion comprises a clear material.

62. Apparatus for use during a procedure in which a tissue graft is inserted into bone tissue, the apparatus comprising an insertion tool for inserting the tissue graft into a bole in the hone tissue, wherein, said insertion tool includes a portion having a length that is adjustable relative to a length of a guide to allow corresponding adjustment of a maximum amount by which the portion may extend from the guide to control a position at which the graft is located in the hole.

* * * * *